US008825503B2

(12) United States Patent
Roizen et al.

(10) Patent No.: US 8,825,503 B2
(45) Date of Patent: Sep. 2, 2014

(54) METHODS AND SYSTEMS FOR IMPROVING HUMAN HEALTH USING TARGETED PROBIOTICS

(75) Inventors: Michael F. Roizen, Shaker Heights, OH (US); Mehmet C. Oz, Cliffside Park, NJ (US)

(73) Assignee: Youdocs, LLC, Shaker Heights, OH (US)

( * ) Notice: Subject to any disclaimer, the term of this patent is extended or adjusted under 35 U.S.C. 154(b) by 540 days.

(21) Appl. No.: 12/466,750

(22) Filed: May 15, 2009

(65) Prior Publication Data

US 2009/0287506 A1 Nov. 19, 2009

Related U.S. Application Data

(60) Provisional application No. 61/053,528, filed on May 15, 2008.

(51) Int. Cl.
G06Q 50/24 (2012.01)
G06Q 99/00 (2006.01)
G06Q 50/22 (2012.01)
G06F 19/00 (2011.01)

(52) U.S. Cl.
CPC .............. *G06F 19/322* (2013.01); *G06Q 50/24* (2013.01); *G06Q 99/00* (2013.01); *G06Q 50/22* (2013.01); *G06F 19/326* (2013.01); *G06F 19/3456* (2013.01)
USPC ............................................................ 705/3

(58) Field of Classification Search
USPC ............................................................ 705/3
See application file for complete search history.

(56) References Cited

U.S. PATENT DOCUMENTS

| | | | | |
|---|---|---|---|---|
| 5,589,168 | A | * | 12/1996 | Allen et al. ................... 424/93.4 |
| 6,589,169 | B1 | * | 7/2003 | Surwit et al. ................... 600/300 |
| 7,162,440 | B2 | * | 1/2007 | Koons ......................... 705/26.35 |
| 7,588,767 | B2 | * | 9/2009 | Szalay et al. ............... 424/199.1 |
| 7,588,771 | B2 | * | 9/2009 | Szalay et al. ............... 424/232.1 |
| 7,662,398 | B2 | * | 2/2010 | Szalay et al. ............... 424/232.1 |
| 2004/0197352 | A1 | * | 10/2004 | Ranganathan ............. 424/234.1 |
| 2006/0172330 | A1 | | 8/2006 | Osborn et al. |
| 2007/0128178 | A1 | * | 6/2007 | Corthesy-Theulaz et al. ........................... 424/93.45 |
| 2007/0214008 | A1 | * | 9/2007 | Jung et al. ......................... 705/2 |
| 2008/0319271 | A1 | * | 12/2008 | Barnowski et al. ........... 600/300 |
| 2010/0135971 | A1 | * | 6/2010 | Schiffrin .................... 424/93.44 |

FOREIGN PATENT DOCUMENTS

WO 2007036230 A1 4/2007

OTHER PUBLICATIONS

Marleen van Nuenen et al., The effect of various inulins and *Clostridium difficile* on the metabolic activity of the human colonic microbiota in vitro. Microbial Ecology in Health and Disease. 2003. 15:137-44.*

Brinich et al., "An analysis of online messages about probiotics," BMC Gastroenterology, 2013, 13:5. (8 pages).*

(Continued)

*Primary Examiner* — Michael Fuelling
(74) *Attorney, Agent, or Firm* — The Marbury Law Group, PLLC

(57) ABSTRACT

Methods and systems enable healthcare providers to identify metabolites that may cause a medical condition in a patient. The healthcare providers may then use the identified metabolite to identify a probiotic that may affect the regulation of that metabolite. Patient information, such as medical history and diagnosis data may then be used in combination with the identified probiotic to create a personalized medicament for that patient.

1 Claim, 4 Drawing Sheets

(56) References Cited

OTHER PUBLICATIONS

International Search Report and Written Opinion of the International Searching Authority, International Application PCT/US2009/044172. International Searching Authority: U.S. Patent and Trademark Office (ISA/US), Jul. 6, 2009.

International Preliminary Report on Patentability, International Application PCT/US2009/044172. International Preliminary Examination Authority: U.S. Patent and Trademark Office (IPEA/US), Sep. 14, 2010.

van Neunen, M., et al. "The effect of various inulins and *Clostridium difficile* on the metabolic activity of the human colonic microbiota in vitro." Microbial Ecology in Health and Disease 2003; 15:137-44.

"Human Metabolic Phenotype Diversity & Its Association with Diet & Blood Pressure," Elaine Holmes, et al., Nature Publishing Group 2008, pp. 1-6.

"Prebiotic (Nutrition)," Wikipedia, May 7, 2009; pp. 1-2.

"Probiotic," Wikipedia, May 15, 2009; pp. 1-14.

"Synbiotics," Wikipedia, May 1, 2009; p. 1.

"What Are Probiotics," usprobiotics.org, 2007, p. 1.

Supplementary European Search Report received from the European Patent Office, International Application No. PCT/US2009/044172 in Application No. EP 09 74 7694 dated Mar. 27, 2014.

van Nuenen, et al., "The Effect of Various Inulins and *Clostridium difficile* on the Metabolic Activity of the Human Colonic Microbiota in vitro", Microbial Ecology in Health and Disease, vol. 69, No. 2-3, pp. 91-144, XP055107907, (Nov. 1, 2003).

\* cited by examiner

METHODS AND SYSTEMS FOR IMPROVING HUMAN HEALTH USING TARGETED PROBIOTICS

CROSS REFERENCE TO RELATED APPLICATIONS

This application claims priority to the provisional patent application No. 61/053,528 which was filed on May 15, 2008. The 61/053,528 application is hereby incorporated by reference in its entirety for all purposes.

BACKGROUND

A host of organisms live in a human body. While all of these organisms benefit from living in a human body, not all of them live in symbiosis with their human host (i.e. are beneficial to their human host). Subsets of the organisms that live in a human body are simply parasitic and do not benefit the human host. A delicate balance between the symbiotic and parasitic organisms keeps the human body in a healthy state. However, when this delicate balance is compromised and the parasitic organisms grow to a critical population, they may cause adverse effects to their human host.

SUMMARY

The various embodiments provide methods and systems for targeting probiotics and personalizing probiotic medicaments for patients. In an embodiment, diagnostic data may be obtained and processed by a health analysis server which is capable of retrieving information from several databases to identify metabolites that may cause the patient's health conditions. One or several metabolites may be identified. A record of the identified metabolites may then be sent to the probiotic server. The probiotic server may also have access to other databases, such as the medical records and probiotic databases. The probiotic server analyzes the identified metabolites and identifies one or several probiotics that may be used to regulate or affect the metabolite production. The probiotics may then be produced and administered to the patient.

In an embodiment, the probiotic server may use patient data such as personal, genetic, ethnic, gender, health, and demographic data to formulate personalize probiotics medicaments for that patient. In this manner, the probiotic medicaments that are formulated for the patient may be most efficacious for that patient.

DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Figure 1:
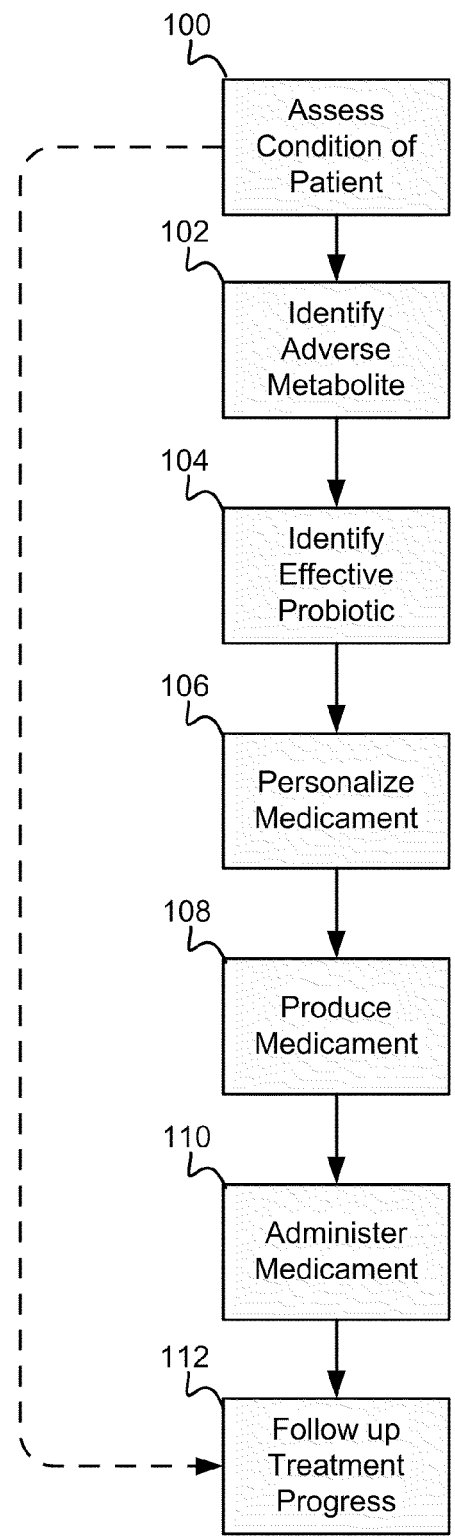
FIG. 1 is a process flow diagram of a method for targeting and personalizing probiotic medicaments according to the various embodiments.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

The term "probiotic" is used herein to mean live microorganisms or their bi-products which when administered in adequate amounts confer a health benefit on the host. The term "prebiotic" is used herein as food ingredients that stimulate the growth and/or activity of bacteria to the digestive system and health of the body. The term "symbiotic" is used herein refer to nutritional supplements combining probiotics and prebiotics to form a synbiotic relationship. The term "metabolite" may be used herein to mean microorganism metabolic products, such as bi-products or waste products, or products of or human body cell metabolism.

The term "health condition" is used herein to include both a healthy state which may be improved and disease states that may receive treatment with respect to a human.

Mammals host many species of microorganisms in their bodies. For example, microorganisms may be found in the alimentary tract, respiratory tract, urinary tract, reproductive tract and on the skin of the host. Some of these microorganisms are beneficial to their mammal host, while others may be harmful.

It has been estimated that a human body hosts tens of trillions of microorganisms, a number that is several times more than the number of living cells in a human body. The relationship between humans and the microorganisms they host is not merely commensal (a non-harmful coexistence), but rather is a mutualistic, symbiotic relationship. For example, microorganisms that reside in the human gut (gut flora) can be beneficial to human health. Though people can survive with no gut flora, the microorganisms perform a host of useful functions, such as fermenting unused energy substrates, training the immune system, preventing growth of harmful species, regulating the development of the gut, producing vitamins for the host (such as biotin and vitamin K), and producing hormones to direct the host to store fats. However, in certain conditions, some species are thought to be capable of causing health conditions by causing infection or increasing the risk of cancer for the host.

Probiotics are suggested to assist the body's naturally occurring microorganisms to re-establish and to keep the body healthy or improve upon the health of an already healthy body. For example, probiotics can help reduce the risk of certain diarrheal illnesses, assist lactose intolerant people with lactose digestion, and enhance the immune function. Some preliminary studies have also reported that certain probiotics can play a role in reducing the development of allergy in children, decreasing *Helicobacter pylori* colonization of the stomach, helping patients cope with side effects of antibiotic therapy, managing relapse of some inflammatory bowel conditions, decreasing the risk of certain cancers, decreasing dental-caries-causing microbes in the mouth, and keeping healthy people healthy. Some commonly used bacteria as probiotics may include *Lactobacillus bifidus* and *Escherichia coli* M-17.

While all humans host many species of microorganisms, each human host has a unique make-up of these microorganisms. As a result of this diversity, different humans may respond differently to diseases and treatments. For example, it was found that individuals who host a certain strain of *Escherichia coli* in their intestines may be resistant to developing enterocolitis during a Shigellosis outbreak. Because each human possesses a unique make-up of microorganism, medical and personal histories, and personal preferences, a "shotgun" approach to treating illnesses with probiotics may not be effective. In other words, when designing a treatment regiment with probiotics, each individual, depending on their unique background, may require different combinations or strains of probiotics, nutrients and nutritional supplements or a combination of the above with other medications or treatments, such as antibiotics or chemotherapy.

In an overview, as illustrated in FIG. 1, the various embodiment methods and systems may enable identifying targeted probiotics for treating individual patient health conditions and for improving a patient's overall health. Additionally, according to the various embodiments, healthcare providers may be enabled to personalize or individualize patient treatments by identifying probiotics and formulating probiotic medicaments that may produce the most beneficial effects for treating a patient's medical condition or for improving the patient's overall health. In doing so, the methods and systems of the various embodiments may allow clinicians to identify nutrient, supplements, medications or therapies that may synergize the effects of the prescribed probiotics and combine the different ingredients to produce a medicament that may provide an optimal effect on the patient's health condition. The medication that may be produced in this manner may be specific to just one individual patient or a group of patients with identical or similar microorganism constitution.

Patients who present with a medical condition may first undergo a health assessment process, block 100. In this process, the health of the patient may be assessed to determine whether the patient may benefit from probiotics. For example, a patient may present without any disease conditions, but the assessment may show that the overall health of the patient may improve by probiotic administration. For example, in an otherwise healthy patient, patient's bowl movement may be regulated to promote a healthier lifestyle and prevent future colonic illnesses. In another example, a patient that presents with a disease condition, such as irritable bowl syndrome, may benefit from probiotic administration for treating his/her illness.

In conducting the health assessment, healthcare providers may ascertain personal and family medical histories, perform a physical exam and perform tests, such as, blood or image tests. They may also perform genetic tests to determine future disease predispositions. In conducting the assessment process, healthcare providers may employ different diagnostic tools. For instance, if a patient complains about gastrointestinal (GI) symptoms, an electronic pill may be prescribed. An electronic pill is a medical device that may be swallowed to collect data from the patient's body and wirelessly send that data to a nearby device servers. Data that may be collected using an electronic pill may include GI pressure, pH, temperature and images. Other tests such as spectroscopic analysis of urine may be used to identify different substances that are present in the urine. Other examples of tests that may be perform include breath tests, for example, to identify the presence of *Helicobacter pylori* in the stomach, and stool and blood analysis and cultures to identify different bacteria that may be present in those organs or human excretes. Diagnostic techniques to identify causes of diseases and to assess the overall health of a patient are well known and may be employed in the various embodiments.

In an embodiment, when a patient has a health condition, the assessment process may identify a definite cause or narrow possible causes to one or a handful of possibilities. By limiting the number of possible causes, clinicians may be able to design targeted probiotic treatments to address their patient's medical issues. In many situations the patient may present with more than one medical complaint, each of which may be manifested by different causes. While it is possible to design a targeted probiotic treatment for one medical condition, the various embodiment methods and systems enable healthcare providers to design holistic probiotic treatments that target all or a collection of a patient's medical problems. In situations where the patient does not present symptoms of a particular illness, the assessment may identify aspects of the patient's overall health that may be improved to either prevent illness or to improve the patient's quality of life.

When the assessment process is completed, the resulting data may be evaluated against a metabolic database using a health analysis server to identify adverse metabolites, block 102. The metabolic database may include information about different metabolites that may be produced in a human body and the organisms that may produce each metabolite. Metabolites may be produced in different ways. For example, microorganisms may produce metabolites (e.g. bi-products or waste products) in the body by metabolizing food or drugs taken by the patient. Similarly, body cells may also produce metabolites by metabolizing substances such as food or drugs. While some metabolites or a certain quantity of some metabolites are beneficial to the body, others types or amounts may cause health conditions in a human body. Additionally, different metabolites affect different human bodies differently. For example, while some metabolites may confer a beneficial effect on a geographic population, the same metabolite may be ineffective in other geographic populations. For example, while hypertension is prevalent worldwide, different parts of the world present with different urine metabolites that may be the cause of their hypertension. A health analysis server may be configured by software instructions to identify metabolites that may cause health conditions in a patient in view of the patient's history, tests, exams and preferences. The health analysis server may also be configured to compare the identified metabolite data to normal ranges for that patient to determine whether the metabolites are the actual causes of the health conditions. Accordingly, the health analysis server may either identify the metabolites that may cause the patient's medical condition, or based on the entirety of the patient's data, such as the patient's diagnostic data, it may suggest performing additional tests or examinations to determine the causing production of metabolites.

When the metabolites responsible for the patient's medical condition are identified, the data may be sent to a probiotic server configured by software instructions to identify a targeted probiotic regiment for that patient, block 104. The probiotic server may identify a targeted probiotic regiment in different ways. For example, a patient's human flora constitution may be known and the data stored as part of the patient's medical record. This means that the type and quantity of different microorganisms in a patient's body may be known. The data may be used by the probiotic server to create a probiotic regiment most compatible with the patient's flora. If all or some of the patient's flora is not known, the probiotic server may use data, such as epidemiologic information, to determine what type of flora may live in the patient. For example, familial, genetic, geographic and/or ethnic information about the patient may be used to group the patient with a population which has the most similar human flora. For example, a first generation Japanese-American patient may be grouped as having human flora known to be prevalent in Japanese patients. As such, the probiotics that may be effective in treating this patient may be different than those used in patients from, for example, Hispanic descent.

Once the most effective probiotics are identified for the patient, the data may be used to personalize a medication for the patient, block 106. The probiotic server may also be configured by software instructions to analyze patient data in view of the targeted probiotic to personalize the patent's medication formulations and regiments. Personalization parameters may include combining prebiotics, nutrients, supplements or other medications simultaneously with the probiotic medication. For example, a probiotic may be administered in combination with an antibiotic in an immunodeficient patent who suffer from an infection in order to increase T-cell lymphocytes while fighting the infection. In these patients antibiotics may be administered simultaneously to synergistically improve the conditions of the patient while attempting to boost the T-cell count.

To personalize probiotic medicaments, different substances may be used as carriers in formulating the probiotic medicaments. For example, in patients with lactose intolerance, the probiotic server may personalize a formulation of a probiotic medicament by using non-dairy products. This reduces patient discomfort during administration of the probiotic medicament while increasing patient compliance with taking the medicament by reducing its adverse side effects.

The route of administration of probiotic medicaments or the state of probiotic may be personalized. For example, to allow more effective results, a probiotic medication may be administered subcutaneously in patients who also suffer from vomiting symptoms. A subcutaneous administration may be more successful since orally administered probiotics may be excreted rapidly out of the system by vomiting before they can manifest their intended effects. In some circumstances, probiotic bi-products or metabolites may be required to treat a medical condition. As such, probiotic bi-products instead of the probiotics may be formulated in the medicament to be administered to achieve the desired effects. Probiotic medicaments may also be personalized by their dosing. For example, a heavier patient may require a higher dose of a probiotic that is administrated subcutaneously. In other embodiments, probiotic medicaments may be produced without the use of any additional substance or carrier.

Once a personalized probiotic medicament is formulated, the formulation data may be used to produce that medication, block 108. For example, if the patient prefers to have a capsule of probiotics, the probiotic medicament may be produced as a capsule. But, if the patient has difficulty swallowing capsules and prefers to take the probiotics with food, the probiotic mediation may be produced as a food item, such as a chocolate bar. Probiotic medicaments may be developed on-site or the formulations may be sent to another location where the medication may be made to order. For example, a hospital may have a probiotic manufacturing section where they can mix probiotics with different food items to administer parentareally to their patients. Alternatively, if more sophisticated techniques may be required to produce the probiotic medication, such as a sterile subcutaneous solution of probiotic bi-products, the formulation may be sent to an off site manufacturer that can produce the medicaments to order and deliver it to the patients quickly.

A follow-up visit may be required to ensure favorable results of a probiotic medication on the patient's medical condition, block 112. During the follow-up visit additional tests may be performed to examine the patient's flora compositions and metabolites and to make any required adjustments in the probiotic medication. Optionally, at the following visit, additional targeted probiotics and personalized probiotic medicament may be identified and prescribed to the patient.

Figure 2:
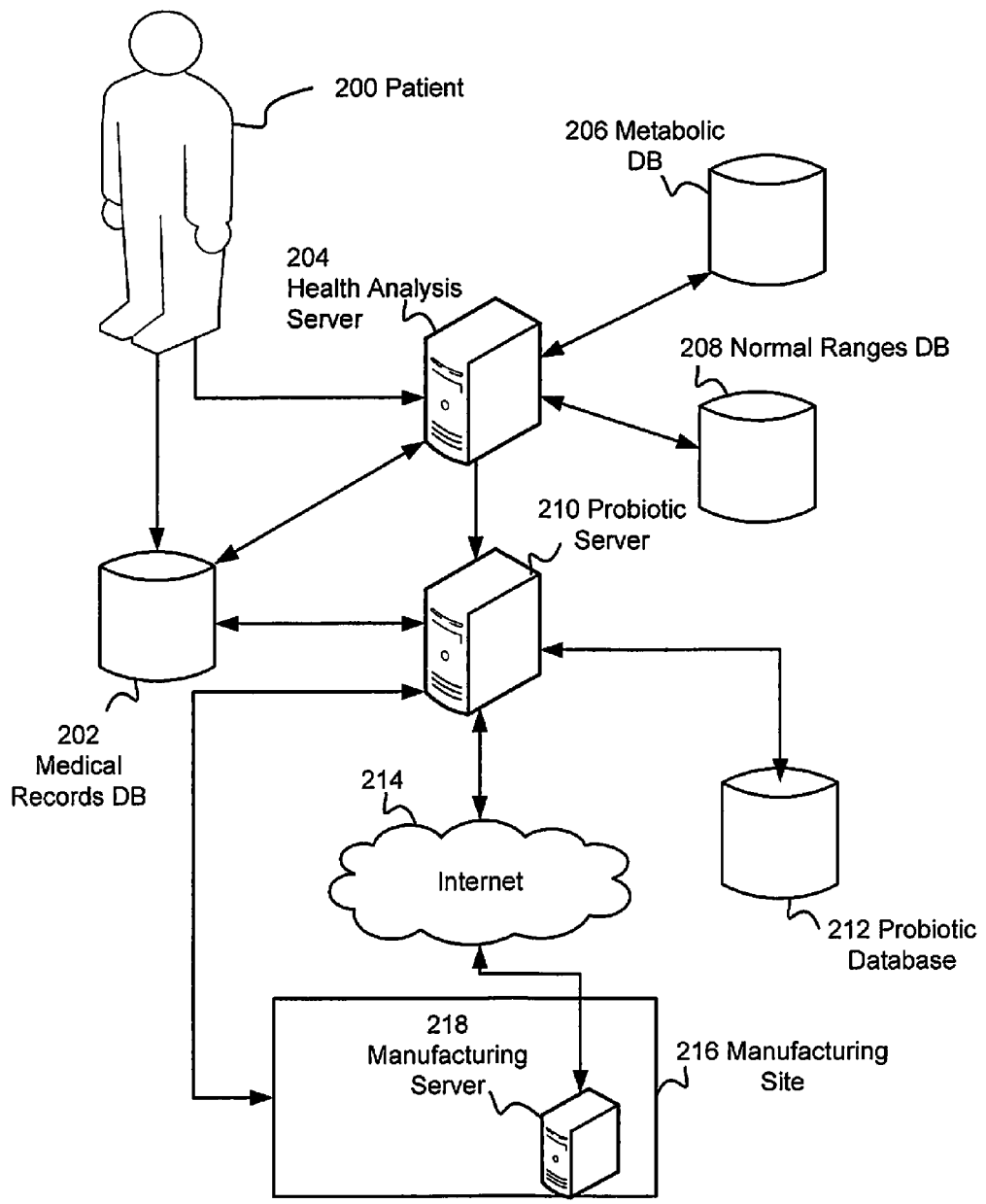
FIG. 2 is a system component diagram illustrating different components of a probiotic medication personalization system according to the various embodiments.

FIG. 2 is a system component diagram illustrating the system components of the probiotic personalization system according to the various embodiments. As illustrated in FIG. 2, patient 200 data may be stored in a medical records database 202. When diagnostic tests are performed on the patients, such as medical imaging or urine analysis, the data may also be stored in the medical database 202. Additionally, the diagnostic data may also be received by the health analysis server 204 directly. The health analysis server 204 may be configured by software to receive and analyze the diagnostic data in view of the patent data to determine the health condition causing metabolites or microorganisms. In doing so, the health analysis server 204 may retrieve data from a metabolite database 206. The metabolite database may include information such as an encyclopedia of different metabolites that may be produced by different microorganisms and a list of health conditions that may be related to different metabolite production or an out of balance microorganism population. The health analysis server 204 may also be configured by software instructions to retrieve normal ranges of metabolites from a normal rages database 208 to determine whether the diagnostic data include any abnormal levels of health condition causing metabolites. The normal ranges database 208 may store information such as normal ranges of metabolites and may categorize them based on population, age, gender, ethnicity or disease conditions. The normal ranges database 208 may also store information such as normal ranges of microorganism populations in different populations, ages, genders, ethnicities or disease conditions. The identified health conditions causing metabolite data generated by the health analysis server 204 may then be sent to a probiotic server 210.

A probiotic server 210 may be configured by software instructions to receive and analyze the resulting metabolite data. In doing so, the probiotic server 210 may be configured by software instructions to retrieve information from a probiotic database 212. The information stored in a probiotic database 212 may include data about different probiotics, the list of health conditions that they may treat individually or in combination with other probiotics or other nutrients, supplements or medications, their effectiveness in different populations, age, gender or race groups, list of probiotic bi-products that may be effective against different health conditions and administrative routes, for example. The probiotic server 210 may also be configured by software to access and retrieve patient medical records. By using data received from the health analysis server 204, the probiotic database 212 and the medical records database 202, the probiotic server 210 may be able to identify a targeted probiotic for an individual patient. The probiotic server 210 may also be able to personalize a probiotic medication and its formulation to the patient being treated. It is well known, that the metabolite and normal ranges databases 206, 208 may be either external or internal to the health analysis server 204. It is also well known that the probiotic database 212 may be internal or external to the probiotic server 210. The arrangements used in FIG. 2 are for example only and are not intended to limit the scope of the various embodiments in the way servers and databases may be arranged and other arrangements are contemplated.

Once a probiotic medicament is formulated, the formulation may be send to a manufacturing site 216. The information may be sent to the medication manufacturing site 216 using the internet 214 or via other connections. The manufacturing site 216 may receive the information at a manufacture server 218. The data received may then be stored and used to manufacture the ordered probiotic medicament. The manufacturing site 216 may be part of the same facility in which the diagnosis and personalization of probiotic medication takes place. Alternatively, the manufacturing site 216 may be located at a remote location. If the manufacturing site 216 is located at a remote location, either the patient may have to travel to that site to retrieve his/her probiotic medication, or the medication may be mailed to the patient. Other arrangements are possible and contemplated.

Figure 3:
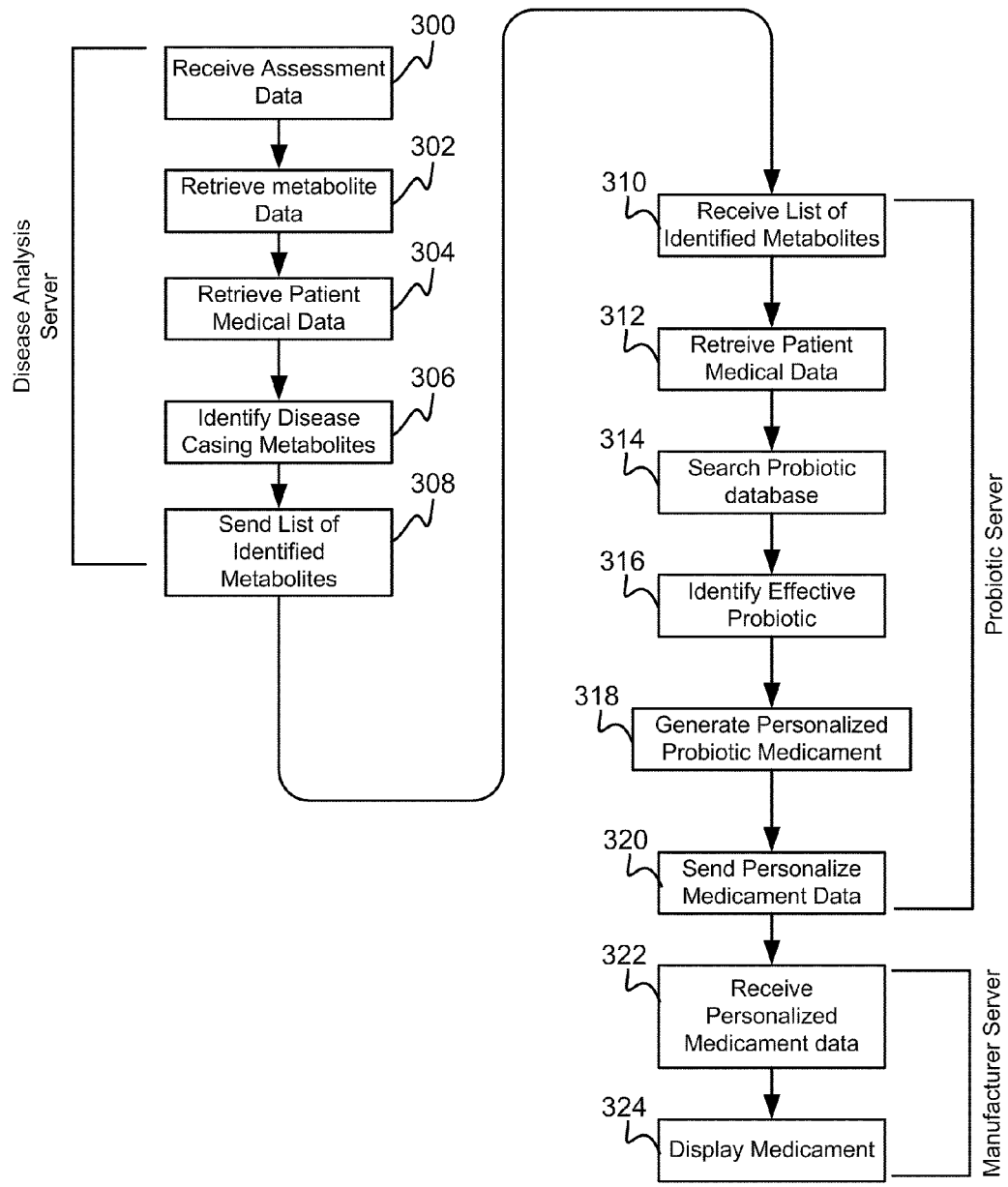
FIG. 3 is a process flow diagram of an exemplary embodiment method for targeting and personalizing probiotic medications.

FIG. 3 is a process flow diagram of an embodiment method for personalizing probiotic medicaments. As illustrated in FIG. 3, the health analysis server 204 may receive assessment data, block 300. Once the assessment data is received, the health analysis server 204 may then retrieve metabolite data, block 302, and patient medication data, block 304. The health analysis server 204 may use the information received to then identify the health condition causing metabolites, block 306. Once the health condition causing metabolites are identified, a list may be generated (block not shown) and the data may be sent to the probiotic server 210, block 308. The probiotic server 210 may then receive the list of identified metabolites, block 310, and retrieve patient data, block 312, from the medical records server 202. The probiotic server 210 may then search the probiotic database 212, block 314, to determine what type or combinations of probiotics may be used to treat the patient's health condition (i.e. suggest a targeted probiotic). Once the effective probiotic (or a combination of probiotics alone or with other substances) is identified, block 316, the probiotic server 210 may use the data received to generate a personalized probiotic medicament formulation, block 318. The personalized formulation may then be sent to the manufacturing server 218, block 320, for production. The manufacturing server 218 may receive the personalized formulation, block 322, and display the formulation for production, block 324.

Figure 4:
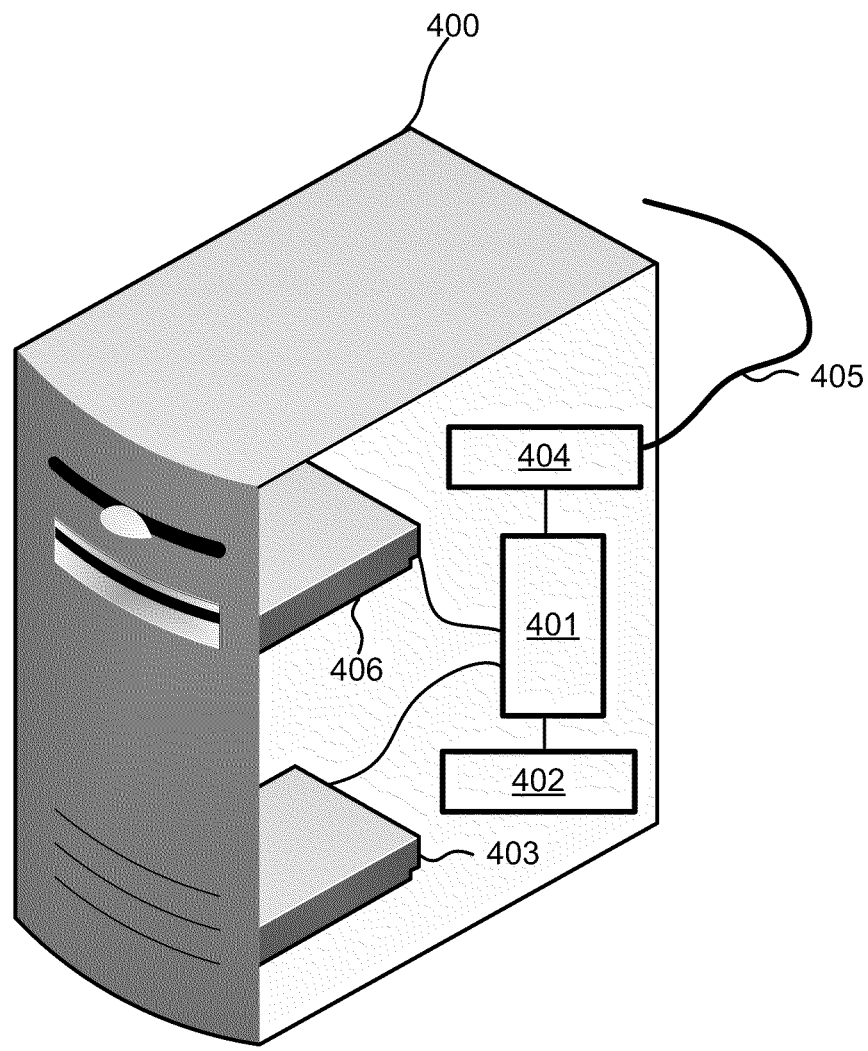
FIG. 4 is a component block diagram of a server device suitable for use in the various embodiments.

A number of the embodiments described above may also be implemented with any of a variety of remote server devices, such as the server 400 illustrated in FIG. 4. Such a server 400 typically includes a processor 401 coupled to volatile memory 402 and a large capacity nonvolatile memory, such as a disk drive 403. The server 400 may also include a floppy disc drive and/or a compact disc (CD) drive 406 coupled to the processor 401. The server 400 may also include network access ports 404 coupled to the processor 401 for establishing data connections with network circuits 405, such as the Internet.

The foregoing method descriptions and the process flow diagrams are provided merely as illustrative examples and are not intended to require or imply that the blocks of the various embodiments must be performed in the order presented. As will be appreciated by one of skill in the art the order of blocks in the foregoing embodiments may be performed in any order. Words such as "thereafter," "then," "next," etc. are not intended to limit the order of the blocks; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some blocks or methods may be performed by circuitry that is specific to a given function.

In one or more exemplary aspects, the functions described may be implemented in hardware, software, firmware, or any combination thereof. If implemented in software, the functions may be stored on or transmitted over as one or more instructions or code on a computer-readable medium. The blocks of a method or algorithm disclosed herein may be embodied in a processor-executable software module executed which may reside on a computer-readable medium. Computer-readable media includes both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a machine readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the invention. Thus, the present invention is not intended to be limited to the embodiments shown herein but is to be accorded the widest scope consistent with the following claims and the principles and novel features disclosed herein.

What is claimed is:

1. A probiotic medication personalization system, comprising:
   a health analysis server comprising:
      a first processor;
      a first network interface coupled to the first processor and configured to connect first the processor to a system network; and
      a first memory storing computer readable instructions which when executed by the first processor cause the first processor to perform operations comprising:
         receiving, via the system network, assessment data from a healthcare provider or a medical database for a medical condition of a patient;
         receiving, via the system network, metabolite data from a metabolite database; and
         identifying, from the metabolite data, a metabolite that affects the medical condition of the patient; and
   a probiotic server comprising:
      a second processor;
      a second network interface configured to connect the probiotic server to the health analysis server via the system network; and
      a second memory storing computer readable instructions which when executed by the second processor cause the second processor to perform operations comprising:
         receiving, from the health analysis server, information about the identified metabolite;
         retrieving patient data from the medical records database and probiotic data from a probiotic database; and
         identifying, from the information about the identified metabolite, the patient data and the probiotic data, a probiotic that regulates the identified metabolite, wherein the probiotic comprises at least one living species of microorganism; and
   a manufacturing site comprising a manufacturing site network interface configured to connect a manufacturing server to the system network, wherein the manufacturing site is configured to perform operations comprising:
      receiving, via the system network, information about the identified probiotic, wherein the information about the identified probiotic is used to manufacture a medicament comprising the identified probiotic.

* * * * *